United States Patent
Elder et al.

(10) Patent No.: US 9,974,726 B2
(45) Date of Patent: May 22, 2018

(54) GENTLE CLEANSING COMPOSITIONS WITH MAKEUP REMOVAL PROPERTIES

(71) Applicant: L'OREAL, Paris (FR)

(72) Inventors: Allison Elder, North Adams, MA (US); Carol Elmasry, South Amboy, NJ (US); David Chan, Edison, NJ (US); Tsung-Hui Marisal Mou, Towaco, NJ (US)

(73) Assignee: L'Oreal, Paris (FR)

(*) Notice: Subject to any disclaimer, the term of this patent is extended or adjusted under 35 U.S.C. 154(b) by 44 days.

(21) Appl. No.: 15/137,880

(22) Filed: Apr. 25, 2016

(65) Prior Publication Data

US 2017/0304173 A1    Oct. 26, 2017

(51) Int. Cl.
| | |
|---|---|
| *A61K 8/46* | (2006.01) |
| *A61K 8/44* | (2006.01) |
| *A61K 8/86* | (2006.01) |
| *A61K 8/41* | (2006.01) |
| *A61Q 19/00* | (2006.01) |
| *A61Q 19/10* | (2006.01) |
| *A61Q 1/14* | (2006.01) |

(52) U.S. Cl.
CPC .............. *A61K 8/466* (2013.01); *A61K 8/416* (2013.01); *A61K 8/442* (2013.01); *A61K 8/86* (2013.01); *A61Q 1/14* (2013.01); *A61Q 19/007* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 9,187,716 B2* | 11/2015 | Griffin | A61K 8/0295 |
| 2009/0062406 A1 | 3/2009 | Loeffler | |
| 2013/0101543 A1* | 4/2013 | Tamareselvy | C08F 2/00 424/70.11 |

FOREIGN PATENT DOCUMENTS

WO    WO-2015/181789 A1    12/2015

OTHER PUBLICATIONS

International Search Report dated Jul. 27, 2017 for corresponding application PCT/US17/29266.

* cited by examiner

*Primary Examiner* — Robert A Wax
*Assistant Examiner* — Melissa S Mercier
(74) *Attorney, Agent, or Firm* — Polsinelli PC (57) ABSTRACT

The present disclosure relates to gentle cleansing compositions, which generally include: (a) a taurate surfactant; (b) an isethionate surfactant; (c) a betaine (and/or another amphoteric surfactant); and (d) a nonionic emulsifier. The cleansing compositions exhibit very good cleansing properties, are particularly effective for removing makeup, and are mild and moisturizing to the skin.

20 Claims, 2 Drawing Sheets

Removability of Long Wear Foundation

* Significance from negative control (D.I. Water) (p = 0.003)

GENTLE CLEANSING COMPOSITIONS WITH MAKEUP REMOVAL PROPERTIES

FIELD OF THE DISCLOSURE

The present disclosure relates to gentle cleansing compositions. The cleansing compositions exhibit very good cleansing properties, are particularly effective for removing makeup, and are mild and moisturizing to the skin.

BACKGROUND

Surfactants are widely used in aqueous based personal care, household, and industrial products. They are typically used as wetting agents, detergents, and emulsifiers. In personal care cleansing products (e.g., shampoos, body washes, facial cleansers, liquid hand soaps, etc.) the surfactant is often the most important component because it provides many of the cleansing attributes of the composition.

Although in principle any surfactant class (e.g., cationic, anionic, nonionic, amphoteric) is suitable in cleansing or cleaning applications, in practice most personal care cleansers and household cleaning products are formulated with anionic surfactants or with a combination of an anionic surfactant as the primary detersive agent with one or more secondary surfactants selected from the other surfactant classes. Anionic surfactants are often used as detersive agents in cleansers and cleaning products because of their excellent cleaning and foaming properties. From the consumer's perspective, the amount and stability of the foam directly relates to the perceived cleaning efficiency of the composition. Generally speaking, the larger the volume of foam produced and the more stable the foam, the more efficient is the perceived cleaning action of the composition. This presents a potential problem in low-surfactant formulations, as foam volume tends to decrease with decreasing surfactant concentration.

Sulfate-based surfactants (such as, for example, sodium lauryl sulfate and sodium lauryl ether sulfate) are particularly popular because of their effectiveness in cleansing, foam production, and stability. Personal care cleansers containing sulfate-based surfactants are also generally easy to thicken with typical thickeners, such as salt and cellulose-based materials. Nonetheless, these particular surfactants can be harsh and irritating to skin. For instance, over-use of sulfate-based surfactants can cause needless drying to the face and scalp, and contribute to color fading and drying of hair. Eliminating sulfate surfactants from cleansing compositions has been challenging because sulfate-free compositions typically have poor foaming properties, are difficult to thicken, are not clear (not transparent). Also, the cleansing ability of sulfate-free composition are often sub-optimal.

SUMMARY OF THE DISCLOSURE

The cleansing compositions of the instant disclosure are surprisingly effective yet mild and moisturizing to the skin. The cleansing compositions are particularly unique in that they are gentle, provide a "clean" and refreshing feel during use, and are surprisingly effective at removing make-up from the skin. Finally, the cleansing compositions are very stable, which is important for providing a long-lasting and durable product for consumers.

The cleansing compositions of the instant disclosure typically include the following:
(a) a taurate surfactant;
(b) an isethionate surfactant;
(c) a betaine; and
(d) a nonionic emulsifier.

In some cases, the taurate surfactant of (a) can be, for example, a compound selected from the group consisting of sodium methyl lauroyl taurate, sodium methyl myristoyl taurate, potassium methyl myristoyl taurate, sodium methyl cocoyl taurate, sodium methyl oleoyl taurate, calcium methyl lauroyl taurate, potassium methyl lauroyl taurate, and ammonium methyl lauroyl taurate.

The isethioniate surfactant of (b) can be, for example, a compound selected from the group consisting of sodium lauroyl isethionate, sodium lauroyl methyl isethionate, sodium myristoyl isethionate, sodium cocoyl isethionate, sodium oleoyl isethionate, and ammonium oleoyl isethionate.

The betaine of (c) can be, for example, coco betaine, cocoamidopropyl betaine, lauryl betaine, laurylhydroxy sulfobetaine, lauryldimethyl betaine, cocoamidopropyl hydroxylsulfo betaine, behenyl betaine, capryl/capramidopropyl betaine, lauryl hydroxysultaine, and stearyl betaine.

Non-limiting examples of nonionic emulsifiers that may be used as (d) include compounds compound selected from the group consisting of polyol esters, glycerol ethers, oxyethylenated and/or oxypropylenated ethers, and ethylene glycol polymers. In some cases, the emulsier includes both a polyol ester and an ethylene glycol polymer.

In addition to the components described above, the cleansing compositions can additionally include: (e) a conditioning polymer. There are many known conditioning polymers that may be used. In some cases, however, the conditioning polymer may be a cationic conditioning polymer. Likewise, in some cases, the conditioning polymer may be selected from the group consisting of a homopolymer or a copolymer derived from acrylic or methacrylic esters or amides, a polysaccharide, a polyamino amide derivative, quaternary diammonium polymers, polyquaternary ammonium polymers, a cationic cellulose or cellulose derivative, and a cationic protein.

The cleansing compositions can also include (f) a rheology modifier (or a thickener). There are many known rheology modifiers. For example, the rheology modifier can be selected from the group consisting of: a polysaccharide; homopolymers of acrylic acid; acrylic acid cross-linked with a polyfunctional compound; hydrophobically-modified copolymers of acrylic acid, acrylate esters, maleic acid and the like; polyethylene glycol units of varying length connected by urethane linkages and terminated with hydrophobic end groups; organoclays; silicas; and fatty alcohols.

The cleansing compositions disclosed herein are particularly useful for cleansing the body, especially the skin. Additionally, the cleansing compositions disclosed herein are useful in methods for removing makeup from the skin. When cleansing and/or removing makeup from the skin, the compositions may be applied to the skin and rinsed from the skin with water. As mentioned above, the cleansing compositions are gentle to the skin and are also unique in their ability to hydrate the skin. Therefore, the compositions may be used in methods for gently hydrating the skin during cleansing.

BRIEF DESCRIPTION OF THE DRAWINGS

Implementations of the present technology will now be described, by way of example only, with reference to the attached figures, wherein.

It should be understood that the various aspects are not limited to the arrangements and instrumentality shown in the drawings.

DETAILED DESCRIPTION OF THE DISCLOSURE

The cleansing compositions of the instant disclosure, in their broadest sense, typically include the following:
(a) a taurate surfactant;
(b) an isethionate surfactant;
(c) a betaine and/or another amphoteric surfactant; and
(d) a nonionic emulsifier.

In some cases, the taurate surfactant of (a) may be, for example, a compound selected from the group consisting of sodium methyl lauroyl taurate, sodium methyl myristoyl taurate, potassium methyl myristoyl taurate, sodium methyl cocoyl taurate, sodium methyl oleoyl taurate, calcium methyl lauroyl taurate, potassium methyl lauroyl taurate, and ammonium methyl lauroyl taurate. Likewise, in some instances, the taurate surfactant is sodium methyl cocoyl taurate.

The taurate surfactant may be present in an amount of 0.1 to 15 wt. %, 0.1 to 12 wt. %, 0.1 to 10 wt. %, 0.1 to 8 wt. %, 0.5 to 15 wt. %, 0.5 to 12 wt. %, 0.5 to 10 wt. %, 0.5 to 8 wt. %, 1 to 15 wt. %, 1 to 12 wt. %, 1 to 10 wt. %, 1 to 10 wt. %, 1 to 8 wt. %, 2 to 10 wt. %, 2 to 8 wt. %, or 2 to 6 wt. %.

In some cases, the isethioniate surfactant of (b) may be, for example, a compound selected from the group consisting of sodium lauroyl isethionate, sodium lauroyl methyl isethionate, sodium myristoyl isethionate, sodium cocoyl isethionate, sodium oleoyl isethionate, and ammonium oleoyl isethionate. Likewise, in some cases, the isethionate surfactant of (b) can be sodium cocoyl isethionate.

The isethionate surfactant may be present in an amount of 0.1 to 15 wt. %, 0.1 to 12 wt. %, 0.1 to 10 wt. %, 0.1 to 8 wt. %, 0.5 to 15 wt. %, 0.5 to 12 wt. %, 0.5 to 10 wt. %, 0.5 to 8 wt. %, 1 to 15 wt. %, 1 to 12 wt. %, 1 to 10 wt. %, 1 to 10 wt. %, or 1 to 8 wt. %.

In addition to the components described above, the cleansing compositions can additionally include (c) a betaine and/or another amphoteric surfactant. Non-limiting examples of amphoteric surfactants include, in addition to betaines, sultaines, amphoacetates, and amphoprorionates. In some cases, when the the amphoteric surfactant is a betaine, suitable betaines include coco betaine, cocoamidopropyl betaine, lauryl betaine, laurylhydroxy sulfobetaine, lauryldimethyl betaine, cocoamidopropylhydroxylsulfo betaine, behenyl betaine, capryl/capramidopropyl betaine, lauryl hydroxysultaine, and stearyl betaine. Finally, there are instances where the amphoteric surfactant is coco betaine.

The betaine and/or another amphoteric surfactant may be present in an amount of 0.1 to 15 wt. %, 0.1 to 12 wt. %, 0.1 to 10 wt. %, 0.1 to 8 wt. %, 0.5 to 15 wt. %, 0.5 to 12 wt. %, 0.5 to 10 wt. %, 0.5 to 8 wt. %, 0.1 to 6 wt. %, 1 to 15 wt. %, 1 to 12 wt. %, 1 to 10 wt. %, 1 to 10 wt. %, 1 to 8 wt. %, 1 to wt. %, 2 to 10 wt. %, 2 to 8 wt. %, or 2 to 6 wt. %.

As mentioned above, the cosmetic compositions typically include (d) a nonionic emulsifier. Non-limiting examples of nonionic emulsifiers that may be used include, for example, compound selected from the group consisting of polyol esters, glycerol ethers, oxyethylenated and/or oxypropylenated ethers, and ethylene glycol polymers. In some cases, the emulsifier includes both a polyol ester or an ethylene glycol polymer, or both a polyol ester and an ethylene glycol polymer, for example, glyceryl stearate and PEG-100 stearate.

The nonionic emulsifier may be present in an amount of 0.01 to 10 wt. %, 0.01 to 8 wt. %, 0.01 to 6 wt. %, 0.01 to 4 wt. %, 0.01 to 2 wt. %, 0.05 to 10 wt. %, 0.05 to 8 wt. %, 0.05 to 6 wt. %, 0.05 to 4 wt. %, or 0.05 to 2 wt. %.

The conditioning polymer of (e) may be any conditioning polymer known in the art. In some cases, however, the conditioning polymer of (e) may be a cationic conditioning polymer. In other cases, the conditioning polymer may be selected from the group consisting of a homopolymer or a copolymer derived from acrylic or methacrylic esters or amides, a polysaccharide, a polyamino amide derivative, quaternary diammonium polymers, polyquaternary ammonium polymers, cationic cellulose or cellulose derivative, and a cationic protein. In some instances, the conditioning polymer is a homopolymer or copolymer derived from acrylic or methacrylic esters or amides, for example, a copolymer of acrylic acid, acrylamide, and methacrylamidopropyltrimonium chloride. Finally, in some cases, the conditioning polymer is a polyquaternium such as, for example, polyquaternium-53.

The conditioning polymer may be present in an amount of 0.01 to 5 wt. %, 0.01 to 4 wt. %, 0.01 to 3 wt. %, 0.05 to 5 wt. %, 0.05 to 4 wt. %, or 0.05 to 3 wt. %

The cleansing compositions can also include (f) a rheology modifier (or a thickener). There are many known rheology modifiers which can be used. For example, the rheology modifier can be a compound selected from the group consisting of polysaccharide units, e.g. cellulose, xanthan gum, diutan gum, carrageenan, gellan gum, welan gum, pectin, sclerotium gum, starch, galactoarabinan, alginate, and modified-forms thereof; homopolymers of acrylic acid; acrylic acid cross-linked with a polyfunctional compound, e.g. carbomer and acrylate crosspolymer; copolymers of acrylic acid, acrylate esters, maleic acid and the like, generally known as the alkali swellable emulsions (ASE) group; hydrophobically-modified copolymers of acrylic acid, acrylate esters, maleic acid and the like, generally known as the hydrophobically-modified alkali swellable emulsions (HASE) group; and polyethylene glycol units of varying length connected by urethane linkages and terminated with hydrophobic end groups, generally known as the hydrophobically-modified ethoxylated urethane resins (HEUR) group; organoclays; silicas; and fatty alcohols.

In some instances, the rheology modifier of (f) may be a selected from the group consisting of cetostearyl alcohol, PEG-14M, xanthan gum, cetyl alcohol, bentonite, carbomer, PEG 12, acrylates/C10-30 alkyl acrylate crosspolymer, konjac mannan, gellan gum, carrageenan, carboxymethyl cellulose, guar gum, rhamsan gum, furcellaran gum, celluloses, polysaccharides, pectin, alginate, and arabinogalactan. The rheology modifier may be, for example, acrylates/C10-30 alkyl acrylate crosspolymer.

The rheology modifier may be present in an amount of 0.01 to 5 wt. %, 0.01 to 4 wt. %, 0.01 to 3 wt. %, 0.01 to 2 wt. %, 0.02 to 5 wt. %, 0.02 to 4 wt. %, 0.02 to 3 wt. % or 0.02 to 2 wt. %.

The cleansing composition described herein may be free or essentially free of one, two, three, or all of sulfates, soaps, fatty alcohols, and/or nonionic surfactants. In some cases, the cleansing compositions are soap free and sulfate free. Alternatively, each of these components may independently and individually (or in combination) be present in amounts less than 5 wt. %, 4 wt. %, 3 wt. %, 2 wt. %, 1 wt. %, 0.5 wt. %, 0.1 wt. %, 0.05 wt. %, or 0.01 wt. %. For example, in some cases, the cleansing compositions are essentially free of sulfates, but include less than the amounts set forth above of nonionic surfactants. Alternatively, the cleansing compositions may comprise less than 2 wt. % of nonionic surfactants and less than 0.5 wt. % of fatty alcohols. Additionally, the cleansing composition may have less than 4 wt. % of a combination of sulfates, soaps, fatty alcohols, and nonionic surfactants.

The cleansing composition may be in the form of an emulsion, e.g., oil-in-water (O/W), water-in-oil (W/O), and oil-in-alcohol emulsions, although the cleansing compositions are often not in the form of an emulsion. The compositions of the instant disclosure may be in the form of a liquid emulsion, such as a liquid-lotion, liquid-gel, liquid-cream, or a cream emulsion, such as a thick cream or gel-cream, or a foam or mousse wherein the liquid emulsion form has a thinner consistency than the cream emulsion form.

The cleansing compositions disclosed herein are particularly useful in methods for cleansing the body, especially the skin, and particularly the skin of the face, wherein the methods comprises applying a composition disclosed herein to the body, skin, and/or face, and rinsing the cleansing composition or wiping-away the composition from the face. Additionally, the cleansing compositions disclosed herein are useful in methods for removing makeup from the skin, especially the skin of the face. The compositions may be applied to the skin and removed from the skin by rinsing. Finally, the compositions may be used in methods for gently hydrating the skin comprising application of the composition to the skin.

More exhaustive but non-limiting lists of components useful in the hair care compositions disclosed herein are presented below.

Taurate Surfactants

The taurate surfactants include those of Formula I, below:

(I)

wherein,
$R^7$ is $(C_8\text{-}C_{22})$alkyl;
$R^8$ is H or $(C_1\text{-}C_4)$alkyl;
$R^9$ and $R^{19}$ are each independently H or $(C_1\text{-}C_4)$alkyl; and
M+ is a sodium, potassium, or ammonium cation.

For example, taurate surfactants include sodium methyl lauroyl taurate, sodium methyl myristoyl taurate, potassium methyl myristoyl taurate, sodium methyl cocoyl taurate, sodium methyl oleoyl taurate, calcium methyl lauroyl taurate, potassium methyl lauroyl taurate, and ammonium methyl lauroyl taurate. Likewise, in some instances, the taurate surfactant is sodium methyl cocoyl taurate.

Isethionate Surfactants

Isethionate surfactants include those according to Formula II, below:

(II)

wherein,
$R^4$ is $(C_5\text{-}C_{22})$alkyl;
$R^5$ and $R^6$ are each independently H or $(C_1\text{-}C_4)$alkyl; and
M+ is a sodium, potassium, or ammonium cation.

For example, isethionate surfactants include sodium lauroyl isethionate, sodium methyl lauroyl isethionate, sodium myristoyl isethionate, sodium cocoyl isethionate, sodium oleoyl isethionate, and ammonium oleoyl isethionate. Likewise, in some cases, the isethionate surfactant of (b) can be sodium cocoyl isethionate.

Amphoteric Surfactants

The at least one amphoteric surfactant useful in the cosmetic compositions disclosed herein is chosen from betaines, sultaines, amphoacetates, amphoprionates, and mixtures thereof. More typically, betaines and amphoprionates are used, and most typically betaines. Betaines which can be used in the current compositions include those having the formulas (XXIIA-D) below:

(XXII A-B)

(XXII C)

(XXII D)

Wherein
$R^{10}$ is an alkyl group having 8-18 carbon atoms; and
n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the invention include the following

(XXIII)

wherein
R is an alkyl group having 8-18 carbon atoms.
Useful alkylamphoacetates include those having the formula (XXIV)

(XXIV)

wherein
R is an alkyl group having 8-18 carbon atoms.
useful alkyl amphodiacetates include those having the formula (XXV)

(XXV)

Wherein
R is an alkyl group having 8-18 carbon atoms.

Emulsifiers

The cosmetic compositions described herein may include one or more emulsifiers. For example the emulsifier may be an amphoteric, anionic, cationic or nonionic emulsifier, used alone or as a mixture. The emulsifiers are chosen in an appropriate manner according to the emulsion to be obtained. The total amount of emulsifiers in the composition are typically in an amount of 0.1 wt. % to 30 wt. %, 0.1 wt. % to 20 wt. %, 0.5 wt. % to 20 wt. %, 1 wt. % to 20 wt. %, 1 wt. % to 15 wt. %, or 1 wt. % to 10 wt. %, or from 0.5, 0.6, 0.7, 0.8, 0.9 or 1.0 wt. % to 5, 6, 7, 8, 9, or 10 wt. %.

As mentioned above, the cosmetic compositions often include a nonionic emulsifier, for example, a compound selected from the group consisting of polyol esters, glycerol ethers, oxyethylenated and/or oxypropylenated ethers, and ethylene glycol polymers. In some cases, the emulsifier includes both a polyol ester or an ethylene glycol polymer, or both a polyol ester and an ethylene glycol polymer, for example, glyceryl stearate and PEG-100 stearate.

O/W emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

W/O emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM90™ by the company Goldschmidt.

In some instance, the one or more emulsifiers include an organosiloxane emulsifier, including crosslinked organosiloxane emulsifiers. For example, the compositions may comprise one or more crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In another embodiment, the compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

Usable oxyalkylenated organosiloxane emulsifier include the following:

An oxyalkylenated organosiloxane emulsifier having the general formula:

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0-25, b is 0-25 with the proviso that both a and b cannot be 0 simultaneously, x, y, and z are each independently ranging from 0 to 1 million with the proviso that x and y cannot be 0 simultaneously. In some cases, x, y, z, a, and b are such that the molecular weight of the polymer ranges from about 5,000 to about 500,000, from about 10,000 to 100,000, or is about 50,000, and the polymer is generically referred to as dimethicone copolyol. In some instances, p is such that the long chain alkyl is cetyl or lauryl, and the the compound is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

An oxyalkylenated organosiloxane emulsifier having the general formula:

wherein each n is independently 0-100 with the proviso that there must be at least one PE radical. In some instances, where each n independently ranges from about 2 to 30, and PE $(-C_2H_4O)_a-(-C_3H_6O)_b-H$ wherein a is 0-25, b is 0-25 with the proviso that both a and b cannot simultaneously be 0; and wherein w, x, y, and z are each independently 0 to 1,000,000 with the proviso that there is at least one PE. In some embodiments the organosiloxane emulsifier is lauryl PEG-9 Polydimethylsiloxyethyl Dimethicone. Oxyalkylenated organosiloxane emulsifiers disclosed in U.S. Pat. No. 9,095,543 are useful in the instant compositions. U.S. Pat. No. 9,095,543 is incorporated herein by reference in its entirety.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially crosslinked oxyalkylenated organosiloxane emulsifiers. They may be elastomeric or non-elastomeric. They are sometimes referred to as "emulsifying elastomers" because of they have both elastomeric and emulsifying properties.

Polyoxyalkylenated silicone elastomers that may be used in at least one embodiment include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers include dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

Conditioning Polymers

The conditioning polymer may be a nonionic polymer, for example, polyalkyloxazolines, vinyl acetate homopolymers, acrylic ester and vinyl acetate copolymers, ethylene and vinyl acetate copolymers, copolymers of vinyl acetate and maleic ester, maleic anhydride and polyethylene copolymers, homopolymers of alkyl acrylates and the homopolymers of alkyl methacrylates, copolymers of acrylic esters, copolymers of acrylonitrile and of a nonionic monomeric unit chosen from butadiene and alkyl (meth)acrylates; and copolymers of alkyl acrylate and urethane.

The conditioning polymer may be a cationic polymer. Cationic conditioning polymers can be chosen from those comprising units of at least one amine group chosen from primary, secondary, tertiary and quaternary amine groups that may either form part of the main polymer chain, or be borne by a side substituent that is directly attached to the main polymer chain. Such cationic polymers generally have a number average molecular mass ranging from 500 to $5 \times 10^6$, or more preferably from 1000 to $3 \times 10^6$. Polymers of the polyamine, polyamino amide and polyquaternary ammonium type that may be used include but are not limited to:

1) homopolymers and copolymers derived from acrylic or methacrylic esters or amides. Copolymers of these polymers can also comprise at least one unit derived from comonomers which may be chosen from the family of acrylamides, methacrylamides, diacetone acylamides, acrylamides and methacrylicamides substituted on the nitrogen with at least one group chosen from lower (C1 C4) alkyls, acrylic and methacrylic acids and esters thereof, vinylactams such as vinlypyrrolidone and vinylcaprolactam, and vinyl esters. Examples of such polymers include:

Copolymers of acrylamide and of methacryloyloxyethyl-trimethylammonium methosulfate, examples of which include polymers known via the INCI nomenclature as Polquaternium-5, such as the products sold under the names Reten 210, Reten 220, Reten 230, Reten 240, Reten 1104, Reten 1105, Reten 1006 by the company Hercules and Merquat 5, Merquat 5 SF by the company Nalco.

Copolymers of vinylpyrrolidone and dimethylaminopropyl methacrylamide, examples of which include polymers known via the INCI nomenclature as Polyquaternium-28, such as the products sold under the name Gafquat HS-100 by the company International Speciality Products (ISP).

Copolymers of vinyl pyrrolidone and dialkyaminoalkyl acrylates or methactylates, examples of which include polymers known via the INCI nomenclature as Polquaternium-11, such as the products sold under the name Gafquat 440, Gafquat 734, Gafquat 755, Gafquat 755N by the company International Speciality Products (ISP), and Luviquat PQ11 PM by the company BASF and Polyquat-11 SL by the company Sino Lion.

Copolymers vinylpyrrolidone, dimethylaminopropyl methacrylamide and methacryloylaminopropyl lauryldimonium chloride, examples of which include polymers known via the INCI nomenclature as polyquaternium-55, such as the products sold under the name Styleze W-20 by the company International Speciality Products (ISP).

Copolymers of acrylic acid, acrylamide and methacrylamidopropyltrimonium chloride, examples of which include polymers known via the INCI nomenclature as Polyquaternium-53, such as the products sold under the name Merquat 2003 by the company Nalco.

Copolymers of dimethyaminopropylacrylate (DMAPA), acrylic acid and acrylonitrogens and diethyl sulfate, examples of which include polymers known via the INCI nomenclature as Polyquaternium-31, such as the products sold under the name Hypan QT100 by the company Lipo.

Copolymers of acrylamide, acrylamidopropyltrimonium chloride, 2-amidopropylacrylamide sulfonate, and dimethyaminopropylacrylate (DMAPA), examples of which include polymers known via the INCI nomenclature as polyquaternium43, such as the products sold under the name Bozequat 4000 by the company Clairant.

Copolymers of acrylic acid, methylacrylate and methacrylamidopropyltrimonium chloride, examples of which include polymers known via the INCI nomenclature as Polyquaternium-47, such as the products sold under the name Merquat 2001 and Merquat 2001N sold commercially by Nalco.

Copolymers of methacryloyl ethyl betaine, 2-hydroxyethyl methacrylate and methacryloyl ethyl trimethyl ammonium chloride, examples of which include polymers known via the INCI nomenclature as Polyquaternium-48, such as the products sold under the name Plascize L450 by the company Goo Chemical.

Copolymers of acrylic acid diallyl dimethyl ammonium chloride and acrylamide, examples of which include polymers known via the INCI nomenclature as polyquaternium 39, such as the products sold under the name Merquat 3330 and Merquat 3331 by the company Nalco.

Further examples include copolymers of methacrylamide methacrylamidopropyltrimonium and methacryloylethyltrimethyl ammonium chloride and their derivatives, either homo or copolymerised with other monomers, examples of which include polymers known via the INCI nomenclature as: Polyquaternium-8, Polyquaternium-9, Polyquaternium-12, Polyquaternium-13 Polyquaternium-14, Polyquaternium-15, such as the products sold under the name Rohagit KF 720 F by the company Rohm, Polyquaternium-30, such as the products sold under the name Mexomere PX by the company Chimex, Polyquaternium-33, Polyquaternium-35, Polyquaternium-36, such as the products sold under the name Plex 3074 L by the company Rhon, Polyquaternium 45, such as the products sold under the name Plex 3073L by the company Rohn, Polyquaternium 49, such as the products sold under the name Plascize L440 by the company Goo Chemicals, Polyquaternium 50 such as the products sold under the name Plascize L441 by the company Goo Chemicals, Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Examples include but are not limited to:

Copolymers of hydroxyethylcelluloses and diallyldimethyl ammonium chlorides, examples of which include polymers known via the INCI nomenclature as Polyquaternium-4, such as the products sold under the name Celquat L 200 and Celquat H 100 by the company National Starch.

Copolymers of hydroxyethylcelluloses and a trimethyl ammonium substituted epoxide, examples of which include polymers known via the INCI nomenclature as Polyquaternium-10, such as the products sold under the name AEC Polyquaternium-10 by the company A&E Connock, Catinal C-100 Catinal HC-35 Catinal HC-100 Catinal HC-200 Catinal LC-100 Catinal LC-200 by the company Toho, Celquat SC-240C Celquat SC-230M, by the company National Starch, Dekaquat 400, Dekaquat 3000 by the company Dekker, Leogard G P by the company Akzo Nobel, RITA Polyquta 400 RITA, Polyquta 3000 by the company RITA, UCARE Polymer JR-125 UCARE Polymer JR-400 UCARE Polymer JR-30M UCARE Polymer LK UCARE Polymer LR 400 UCARE Polymer LR 30M by the company Amerchol.

Copolymers of hydroxyethylcelluloses and lauryl dimethyl ammonium substituted epoxides, examples of which include polymers known via the INCI nomenclature as Polyquaternium-24, such as the products sold under the name Quatrisoft polymer LM-200 by the company Amerchol.

Derivatives of Hydroxypropyl Guar, examples of which include polymers known via the INCI nomenclature as Guar Hydroxypropyltrimonium Chloride, such as the products sold under the name Catinal CG-100, Catinal CG-200 by the company Toho, Cosmedia Guar C-261N, Cosmedia Guar C-261N, Cosmedia Guar C-261N by the company Cognis, DiaGum P 5070 by the company Freedom Chemical Diamalt, N-Hance Cationic Guar by the company Hercules/Aqualon, Hi-Care 1000, Jaguar C-17, Jaguar C-2000, Jaguar C-13S, Jaguar C-14S, Jaguar Excel by the company Rhodia, Kiprogum CW, Kiprogum NGK by the company Nippon Starch.

Hydroxypropyl derivatives of Guar Hydroxypropyltrimonium Chloride, examples of which include polymers known via the INCI nomenclature as Hydroxypropyl Guar Hydroxypropyltrimonium Chloride, such as the products sold under the name Jagaur C-162 by the company Rhodia.

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Non-limiting examples of such derivatives include the adipic acid/epxoypropyl/diethylenetriamine.

5) Cyclopolymers of dialkdiallylamine or of dialkyldiallyammonium, among which polymers mention may be made of:

Dimethyldiallyammonium chloride polymers, examples of which include polymers known via the INCI nomenclature as Polyquaternium-6, such as the products sold under the name Merquat 100 by the company Nalco, Mirapol 100 by the company Rhodia, Rheocare CC6 by the company Cosmetic Rheologies, AEC polyquaternium-6 by the company A&E Connock, Agequat 400 by the company CPS, Conditioner P6 by the company 3V Inc., Flocare C106 by the company SNF, Genamin PDAC by the company Clariant, Mackernium 006 by the company McIntyre.

Copolymers of acrylamides and dimethyldiallyammonium chlorides monomers, examples of which include polymers known via the INCI nomenclature as Polyquaternium-7, such as the products sold under the name AEC Polyquaternium-7 by the company A&E Connock, Agequat-5008, Agequat C-505 by the company CPS, Conditioner P7 by the company 3V Inc. Flocare C 107 by the company SNF Mackernium 007, Mackernium 007S by the company McIntyre, ME Polymer 09W by the company Toho, Merquat 550, Merquat 2200, Merquat S by the company Nalco, Mirapol 550 by the company Rhodia, Rheocare CC7, Rheocare CCP7 by the company Cosmetic Rheologies, Salcare HSP-7, Salcare SC10, Salcare Super 7 by the company Ciba.

Copolymers of dimethyldiallylammoniumchlorides and acrylic acids, examples of which include polymers known via the INCI nomenclature as polyquaternary-22, such as the products sold under the name Merquat 280 and Merquat 295 by the company Nalco.

6) Quaternary diammonium polymers comprising repeat units corresponding to [—N—F(R1)(R2)-A1-N+(R3)(R4)-B1-][2X—], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other than nitrogen, or R1, R2, R3 and R4, are chosen from liner or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. An example of which include polymers known via the INCI nomenclature as Hexadimethrine chloride, where R1, R2, R3 and R4 are each methyl radicals, A1 is $(CH_2)_3$ and B1 is $(CH_2)6$ and X=C1. Further examples of which include polymers known via the INCI nomenclature as polyquaternium-34 where R1 and R2 are ethyl radicals and R3 and R4 are methyl radicals and A1 is (CH2)3 and B1 is (CH2)3 and X=Br, such as the products sold under the name Mexomere PAX by the company Chimax.

7) Polyquaternary ammonium polymers comprising repeating units of formula [—N+(R6)(R7)-(CH2) r-NH—CO—(CH2)q-(CO)t-NH—(CH2)s-N+(R8)(R9)-A-][2X—], in which R6, R7, R8 and R9 which may be identical or different, are chosen from a hydrogen atom and a methyl, ethyl, propyl, hydroxyethyl, hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —CH2-CH2-O—CH2-CH2-. Examples of which include:

Polymers known via the INCI nomenclature as polyquaternium-2, where r=s=3, q=0, t=0, R6, R7, R8 and R9 are methyl groups, and A is —CH2-CH2-O—CH2-CH2, such as the products sold under the name Ethpol PQ-2 from Ethox and Mirapol A-15 by the company Rhodia.

Polymers known via the INCI nomenclature as polyquaternium-17 where r=s=3, q=4, t=1 R6, R7, R8 and R9 are methyl groups, and A is —CH2-CH2-O—CH2-CH2.

Polymers known via the INCI nomenclature as Polyquaternium 18, where r=s=3, q=7, t=1 R6, R7, R8 and R9 are methyl groups, and A is —CH2-CH2-O—CH2-CH2

Polymers known via the INCI nomenclature as the block copolymer formed by the reaction of Polyquaternium-2 with Polyquaternium-17, known as Polyquaternium 27, such as the products sold under the name Mirapol 175 by the company Rhodia.

8) Copolymers of vinylpyrrolidones and of vinylimidazoles and optionally vinylcaprolactums, examples of which include polymers known via the INCI nomenclature as Polyquaternary-16 formed from methylvinylimidazolium chlorides and vinylpyrrolidones, such as the products sold under the name Luviquat FC370, Luviquat FC550, Luviquat FC905, Luviquat HM-552 by the company BASF. Or copolymers of vinylcaprolactams and vinylpyrrolidones with methylvinylimidazolium methosulfates, examples of which include polymers known via the INCI nomenclature as Polyquaternium-46, such as the products sold under the name Luviquat Hold by the company BASF. Or copolymers of vinylpyrrolidones and quaternized imidazolines, examples of which include polymers known via the INCI nomenclature poylquaterary 44, such as the products sold under the name Luviquat Care by the company BASF 9) Polyamines such as the product Polyquart H sold by Cognis under the reference name polyethylene glycol (15) tallow polyamine in the CTFA dictionary.

10) Cross linked methacryloyloxy(C1-C4)alkyltri(C1-C4)alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, examples of which include polymers known via the INCI nomenclature as Polyquaternium-37, such as the products sold under the name Synthalen, CN Synthalen CR, Synthalen CU, sold by 3V sigma, or as a dispersion in another media such as the products sold under the name Salcare SC95 and Salcare SC96 by the company Ciba or Rheocare CTH(E) by the company Cosmetic Rheologies. Or in another example of which include polymers known via the INCI nomenclature as Polyquaternium-32, or when sold as a dispersion in mineral oil such as the products sold under the name Salcare SC92 by the company Ciba.

11) Further examples of cationic polymers include polymers known via the INCI nomenclature as Polyquaternium 51, such as the products sold under the name Lipidure-PMB by the company NOF, via the INCI nomenclature as Polyquaternium 54, such as the products sold under the name Qualty-Hy by the company Mitsui, and via the INCI nomenclature as Polyquaternium 56 such as the products sold under the name Hairrol UC4 by the company Sanyo chemicals.

12) Silicone polymers comprising cationic groups and/or groups which may be ionised into cationic groups. For example: cationic silicones of the general formula (R10-N+(CH3)2)-R11-(Si(CH3)2-O)x-R11-(N+(CH3)2)-R10), where R10 is an alkyl derived from coconut oil, and R11 is (CH2CHOCH2O(CH2)3 and x is a number between 20 and 2000, examples of which include polymers known by the INCI nomenclature as Quaternium 80, such as the products sold under the name as Abil Quat 3272 and Abil Quat 3474 sold commercially by Goldschmidt.

Silicones containing groups which may be ionised into cationic groups, for example aminosilicones containing at least 10 repeating siloxane —(Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12(CH3)2Si—O, where R12 can be either OH or OR13, where R13 is a C1 C8 alky group, or a mixture of both functional terminal groups. These silicones are also available as preformed emulsions. Polymer with terminal siloxane units of (CH3)3Si—O examples of which include polymers known by the INCI nomenclature as trimethylsilylamodimethicone, such as the products sold under the name as DC-2-8566, DC 7224 and DC-2-8220 sold commercially by Dow Corning and SF1708 and SM 2125 sold commercially by GE Silicones and Wacker Belsil ADM 653 sold commercially by Wacker silicones. Further examples include polymers with terminal siloxane units of (R120)(CH3)2Si—O where R12 can be either OH or OR13, where R13 is a C1 C8 alky group, or a mixture of both functional terminal groups, known by the INCI nomenclature as amodimethicone, such as the products sold under the name as Wacker Belsil ADM 1100, Wacker Belsil ADM 1600, Wacker Belsil ADM 652, Wacker Belsil ADM 6057E, Wacker Belsil ADM 8020 sold commercial by Wacker Silicones, DC929, DC939 and DC949 sold commercially by Dow Corning and SM2059 sold commercially by GE silicones.

Silicones containing groups which may be ionised into cationic groups—for example silicones containing at least 10 repeating siloxane —Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products know by the INCI nomenclature as methoxy PEG/PPG-7/3 Aminopropyl Dimethicone, such as the product sold under the name of Abil Soft AF100 sold commercially by Degussa. For example products know by the INCI nomenclature as Bis (C13 15 Alkoxy) PG Amodimethicone, such as the product sold under the name of DC 8500 sold commercially by Dow Corning.

Rheology Modifiers

Consumers expect of their cleansing products have an aesthetically pleasing viscosity. Formulations that flow with a watery consistency are aesthetically unpopular to consumers with expectations of rich and creamy products. While low viscosity products may be effective for their intended purpose, they are perceived to be of low quality by the consumer. Formulations that flow with a watery consistency run off when applied.

Rheology modifiers are used in aqueous cleansing products to manipulate the viscosity, usually to increase the viscosity to make them easier for the user to handle and/or to increase the yield stress of the composition. While a certain rheology modifiers may thicken or enhance the viscosity of a composition in which it is included, it may not necessarily have desirable yield stress properties. A desirable yield stress property is critical to achieving certain physical and aesthetic characteristics in a liquid medium, such as overall formula stability. An acceptable yield stress value can impart a formula with adequate shelf life stability. It can also help suspend particles, insoluble liquid droplets, or gas bubbles within a liquid medium. Particles dispersed in a liquid medium will remain suspended if the yield stress (yield value) of the medium is sufficient to overcome the effect of gravity or buoyancy on those particles. Insoluble liquid droplets can be prevented from rising and coalescing and gas bubbles can be suspended and uniformly distributed in a liquid medium using yield value as a formulating tool. A yield stress fluid is used generally to adjust or modify the rheological properties of aqueous compositions. Such properties include, without limitation, viscosity improvement, flow rate improvement, stability to viscosity change over time, and the ability to suspend particles for indefinite periods of time.

The cosmetic compositions described herein may include a rheology modifier. The rheology modifier may be in an amount of 0.1 wt. % to 20 wt. %, 0.1 to 10 wt. %, 0.1 wt. % to 9 wt. %, 0.2 wt. % to 9 wt. %, 0.3 wt. % to 9 wt. %, 0.4 wt. % to 8 wt. %, 0.5 wt. % to 5 wt. %, 1 wt. % to 5 wt. %, or 2 wt. % to 4 wt. %. Further, the amount of thickener may be from 0.1, 0.2, 0.3, 0.4, 0.5, 0.6, 0.7, 0.8, 0.9, 1.0, or 1.5 wt. % to 2, 3, 4, 5, 6, 7, 8, 9, 10, 15, or 20 wt. %.

The rheology modifier may be xanthan gum, guar gum, biosaccharide gum, cellulose, acacia Seneca gum, sclerotium gum, agarose, pechtin, gellan gum, hyaluronic acid. Additionally, the rheology modifier may include polymeric thickeners selected from the group consisting of ammonium polyacryloyldimethyl taurate, ammonium acryloyldimethyl-taurateNP copolymer, sodium polyacrylate, acrylates copolymers, polyacrylamide, carbomer, and acrylates/C10-30 alkyl acrylate crosspolymer. In some cases, the composition includes ammonium polyacryloyldimethyl taurate and/or sodium polyacrylate.

Many thickeners are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol™ 900 series from B.F. Goodrich (e.g., Carbopol® 954). In addition, other suitable carboxylic acid polymeric agents include Carbopol Ultrez® 20 (Lubrizol Corp.), which is acrylates/$C_{10}$-$C_{30}$ alkyl acrylate crosspolymer, Ultrez® 10 (B.F. Goodrich), and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. No. 5,100,660, U.S. Pat. No. 4,849,484, U.S. Pat. No. 4,835,206, U.S. Pat. No. 4,628,078 U.S. Pat. No. 4,599,379 and EP 228,868, which are all incorporated herein by reference in their entirety.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation. An exemplary polyacrylamide polymers is, for example, ammonium polyacryloyldimethyl taurate (Clariant Hostacerin AMPS).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

d. Gums and Polysaccharides

A wide variety of gums and polysaccharides can be useful herein as gelling agents. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation. Further polysaccharides include starch derivatives (for example, starch oxide, dialdehyde starch, dextrin, British gum, acetyl starch, starch phosphate, carboxymethyl starch, hydroxyethyl starch, hydroxypropyl starch).

Other useful polysaccharides include scleroglucans comprising a linear chain of (1-3) linked glucose units with a (1-6) linked glucose every three units, a commercially available example of which is Clearogel™. CS11 from Michel Mercier Products Inc.

Other thickening and gelling agents useful herein include materials which are primarily derived from natural sources. Nonlimiting examples of these gelling agents are gums such as acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Implementation of the present disclosure is provided by way of the following examples. The examples serve to illustrate the technology without being limiting in nature.

Example 1

Cleansing Compositions

| Claim Component | INCI US Name | A | B | C |
|---|---|---|---|---|
| (a) | Sodium methyl cocoyl taurate | 4.5 | 3.6 | 2.3 |
| (b) | Sodium cocoyl isethionate | 1.8 | 2.8 | 1.8 |
| (c) | Coco betaine | 3 | 1.5 | 2.2 |
| (d) | Peg-100 Stearate/Glyceryl stearate | 1 | 1 | 0.6 |
| (e) | Polyquaternium | 0.1 | 0.4 | 0.7 |
| (f) | Rheology modifier | 0.5 | 0.5 | 0.5 |
| | Glycerin | 5 | 5 | 5 |
| | Preservatives, pH Adjusters, co-solvents, and fragrances | 1-5 | 1-5 | 1-5 |
| | Water | Q.S. 100 | Q.S. 100 | Q.S. 100 |

Figure 1:
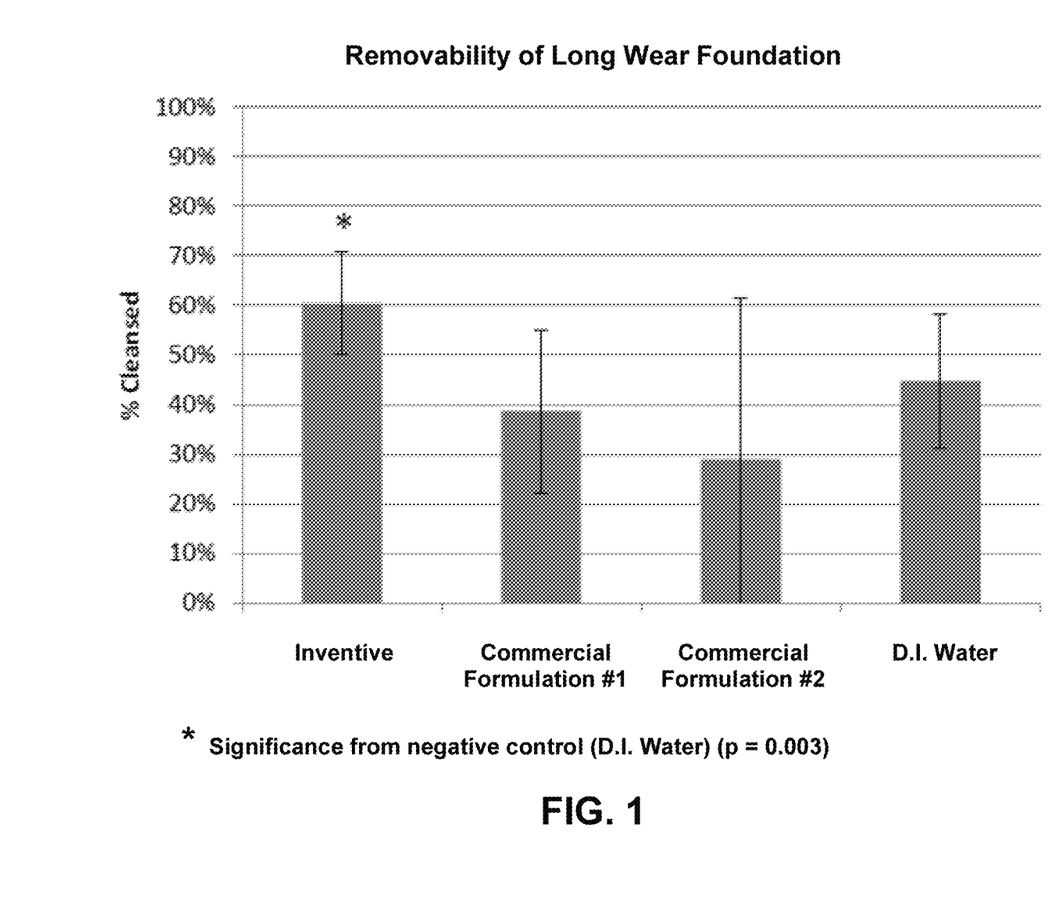
FIG. 1 is a graph comparing an inventive gentle cleansing composition's ability to remove long wear foundation with that of two commercially available gentle cleansing compositions and D.I. water (negative control)
Figure 2:
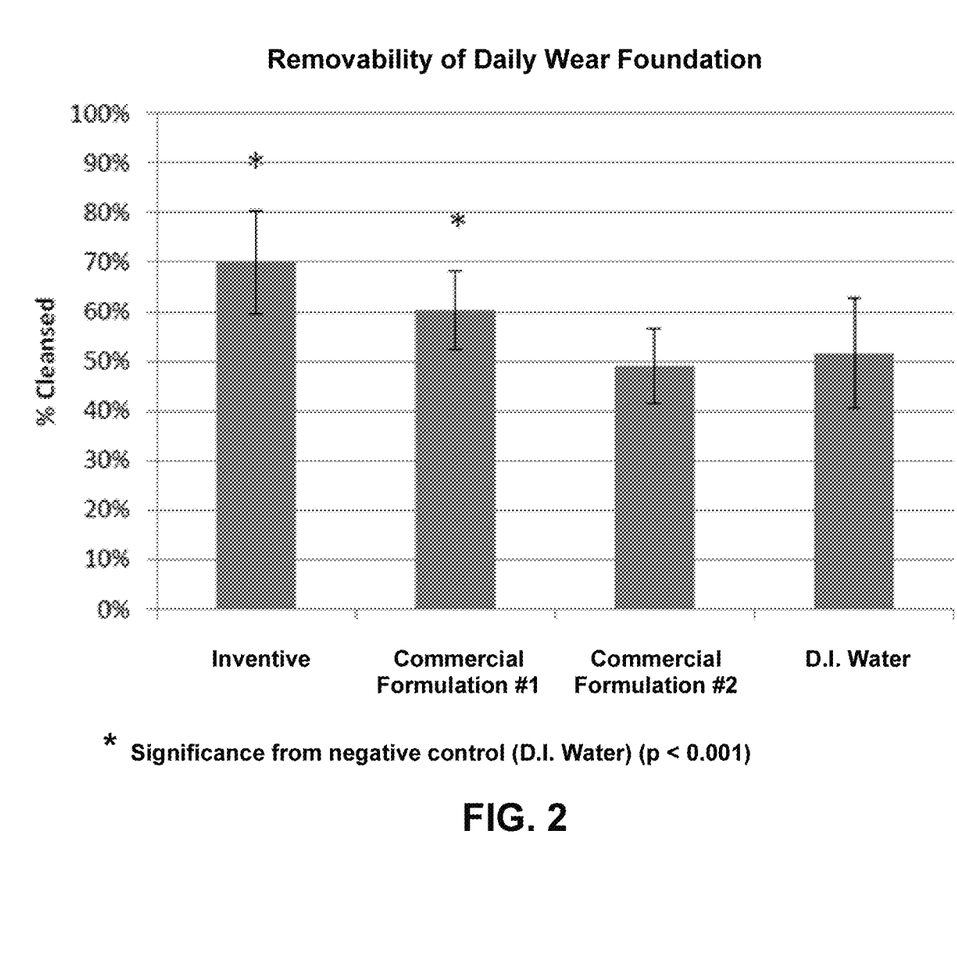
FIG. 2 is a graph comparing an inventive gentle cleansing composition's ability to remove daily wear foundation with that of two commercially available gentle cleansing compositions and D.I. water (negative control).

A small amount of makeup (either a long wear foundation or a daily wear foundation) was applied to a circular area on the forearm of eighteen different women. The initial color intensity of the makeup on the forearm was assessed. Then, the forearms treated with makeup were washed using an inventive gentle cleansing composition (according to the instant disclosure) or with other commercial gentle cleansing compositions. After cleansing, the color of the forearms was again evaluated. Less residual color corresponds to better makeup removal (i.e., higher % cleansed). The results are presented in the below tables and graphically presented in FIG. 1 (long wear foundation) and FIG. 2 (daily wear foundation).

| Removability of Long Wear Foundation | |
|---|---|
| Formula | Percent Cleansed |
| Inventive Formulation | 60.4% |
| Commercial Formulation #1 | 38.7% |
| Commercial Formulation #2 | 29.0% |
| D.I. Water | 44.7% |

| Removability of Daily Wear Foundation | |
|---|---|
| Formula | Percent Cleansed |
| Inventive Formulation | 70.0% |
| Commercial Formulation #1 | 60.3% |
| Commercial Formulation #2 | 49.1% |
| D.I. Water | 51.6% |

The inventive formulation performed significantly better than both commercial gentle cleansing compositions (and better than D.I. Water) in its ability to remove makeup (both long wear foundation and daily wear foundation).

Example 2

Zein Solubility Test

The purpose of the Zein Solubility Test is to investigate the irritation potential (harshness) of a surfactant-based product. A high percent Zein Score represents irritation and harshness. A low percent Zein Score represents mildness and lack of irritation. Zein is a yellow corn protein that is similar to the keratin present in skin. It has limited solubility in water and is denatured (solubilized) by surfactants. The ability of surfactants to denature and solubilize zein has been linked to a surfactant's skin-irritation potential. The soluble zein protein is determined by utilizing a standard protein assay which measures protein absorbance values using a spectrophotometer. The amount of absorption correlates with the harshness of the product. The samples were tested and the results reported relative to a 5% solution of sodium lauryl sulfate (SLS), as a positive control. The Zein Scores are expressed in terms of percentage of the SLS Zein Score.

| Surfactant | Product | % Zein Score |
|---|---|---|
| Sodium lauryl sulfate | 5% sodium lauryl sulfate | 100 |
| Soap | Commercial Soap Face Wash #1 | 90.8 |
| | Commercial Soap Face Wash #2 | 87.7 |
| | Commercial Soap Face Wash #3 | 84.5 |
| | Commercial Soap Face Wash #4 | 81.1 |
| | Commercial Soap Face Wash #5 | 77.0 |
| | Commercial Soap Face Wash #6 | 75.4 |
| Soap + Anionic Surfactant | Commercial Soap and Anionic Surfactant Face Wash #1 | 74.7 |
| | Commercial Soap and Anionic Surfactant Face Wash #1 | 50.7 |
| Anionic Surfactant | Commercial Soap and Anionic Surfactant Face Wash #2 | 39.8 |
| Anionic Surfactant + Amino Anionic Surfactant | Comparative Formula | 20.17 |
| | Comparative Formula | 14.7 |
| Amphoteric Surfactant | Commercial Amphoteric Surfactant Face Wash #1 | 10.8 |
| Taurate Surfactant + Isethionate Surfacant | Example 1 (Inventive Composition) | 6.2 |

Example 3

Hydration Test

Each of the compositions in the table below were individually applied to the skin of an arm (n=10) and then removed with a moist cotton pad. A corneometer was used to take initial measurements, and subsequent measurements at 1, 2, and 6 hour time points.

|  | Product | 0 hours | 1 hours | 2 hours | 6 hours |
| --- | --- | --- | --- | --- | --- |
| Cleansing Comparisons | Example 1 (Inventive Composition) | 33.1 | 36.3* | 37.0* | 36.2 |
|  | Commercial gentle facial cleanser #1 | 33.2 | 35.5 | 35.0 | 32.9 |
|  | Commercial gentle facial cleanser #2 | 31.6 | 32.5 | 32.6 | 34.0 |
|  | 5% sodium lauryl sulfate (Common cleansing detergent) | 30.7 | 34.2 | 33.5 | 32.4 |
| Controls | Commercial Moisturizer (not a cleanser) (Positive Control) | 33.3 | 49.1* | 47.1* | 41.5* |
|  | Untreated Skin (Negative Control) | 30.7 | 31.7 | 31.6 | 32.6 |

*Statistically significant

The data show that only the inventive composition of Example 1 significantly hydrated the skin at 1 hour and 2 hour time points after cleansing. The competitor products, 5% SLS, and untreated skin did not demonstrate 1 or 2 hour skin hydration.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cleansing composition comprising 50 to 92 wt. % water, and:
   a. 1 to 15 wt. % of a taurate surfactant;
   b. 0.1 to 15 wt. % of an isethionate surfactant;
   c. 0.1 to 15 wt. % wt. % of a betaine; and
   d. 0.01 to 10 wt. % of a nonionic emulsifier selected from the group consisting of a polyol ester, a glycerol ether, an oxyalkylenated fatty acid ether, an oxyalkylenated fatty acid ester, and a mixture thereof;
   wherein the composition is essentially free of sulfates.

2. The cleansing composition of claim 1, wherein the taurate surfactant of (a) a compound selected from the group consisting of sodium methyl lauroyl taurate, sodium methyl myristoyl taurate, potassium methyl myristoyl taurate, sodium methyl cocoyl taurate, sodium methyl oleoyl taurate, calcium methyl lauroyl taurate, potassium methyl lauroyl taurate, and ammonium methyl lauroyl taurate.

3. The cleansing composition of claim 2, wherein the taurate surfactant is sodium methyl cocoyl taurate.

4. The cleansing composition of claim 1, wherein the isethionate surfactant of (b) a compound selected from the group consisting of sodium lauroyl isethionate, sodium lauroyl methyl isethionate, sodium myristoyl isethionate, sodium cocoyl isethionate, sodium oleoyl isethionate, and ammonium oleoyl isethionate.

5. The cleansing composition of claim 4, wherein the isethionate surfactant is sodium cocoyl isethionate.

6. The cleansing composition of claim 1, wherein the betaine of (c) is selected from the group consisting of coco betaine, cocoamidopropyl betaine, lauryl betaine, laurylhydroxy sulfobetaine, lauryldimethyl betaine, cocoamidopropylhydroxylsulfo betaine, behenyl betaine, capryl/capramidopropyl betaine, lauryl hydroxysultaine, and stearyl betaine.

7. The cleansing composition of claim 6, wherein the betaine is coco betaine.

8. The cleansing composition of claim 1, wherein the nonionic emulsifier of (d) comprises a polyol ester and an oxyalkylenated fatty acid ester.

9. The cleansing composition of claim 8, wherein the nonionic emulsifier of (d) comprises glyceryl stearate and PEG-100 stearate.

10. The cleansing composition of claim 1, further comprising:
    e. a conditioning polymer.

11. The cleansing composition of claim 10, wherein the conditioning polymer of (e) is selected from the group consisting of a homopolymer or a copolymer derived from acrylic or methacrylic esters or amides, a polysaccharide, a polyamino amide derivative, quaternary diammonium polymers, polyquaternary ammonium polymers, a cationic cellulose or cellulose derivative, and a cationic protein.

12. The cleansing composition of claim 11, wherein the conditioning polymer of (e) is homopolymer or copolymer derived from acrylic or methacrylic esters or amides.

13. The cleansing composition of claim 12, wherein the conditioning polymer of (e) is a copolymer of acrylic acid, acrylamide, and methacrylamidopropyltrimonium chloride.

14. The cleansing composition of claim 11, further comprising:
    (f) a rheology modifier.

15. A cleansing composition comprising 50 to 92 wt. % water:

(a) 1 to 15 wt. % of a tauruate surfactant;
(b) 0.1 to 15 wt. % of an isethionate surfactant;
(c) 0.1 to 15 wt. % of a betaine;
(d) 0.01 to 10 wt. % of a nonionic emulsifier selected from the group consisting of a polyol ester, a glycerol ether, an oxyalkylenated fatty acid ether, an oxyalkylenated fatty acid ester, and a mixture thereof;
(e) 0.01 to 5 wt. % of a polyquaternium; and
(f) 0.01 to 5 wt. % of a rheology modifier;
wherein the composition is essentially free of sulfates.

16. A method for cleansing the face comprising applying the cleansing composition of claim 1 to the face, thereby cleansing the face.

17. A method for removing makeup from skin comprising applying the cleansing composition of claim 1 to skin upon which makeup has already been applied, thereby removing the makeup from the skin.

18. A cleansing composition of claim 15, wherein the nonionic emulsifier of (d) comprises a polyol ester and an oxyalkylenated fatty acid ester.

19. A cleansing composition of claim 15 comprising:
(a) 1 to 15 wt. % of sodium methyl cocoyl taurate;
(b) 0.1 to 15 wt. % of sodium cocoyl isethionate;
(c) 0.1 to 15 wt. % of coco betaine;
(d) 0.01 to 10 wt. % of glyceryl stearate and PEG-100 stearate;
(e) 0.01 to 5 wt. % of a polyquaternium; and
(f) 0.01 to 5 wt. % of a homopolymer or copolymer derived from acrylic or methacrylic esters or amides.

20. A cleansing composition of claim 19, wherein the polyquaternium is polyquaternium-53.

* * * * *